(12) United States Patent
Eyal et al.

(10) Patent No.: US 10,010,253 B2
(45) Date of Patent: Jul. 3, 2018

(54) SLEEP ANALYSIS BASED ON INTER BEAT INTERVAL

(75) Inventors: Shulamit Eyal, Givat Shmuel (IL); Armanda Lia Baharav, Tel-Aviv (IL)

(73) Assignee: HypnoCore Ltd., Petach-Tikva (IL)

( * ) Notice: Subject to any disclaimer, the term of this patent is extended or adjusted under 35 U.S.C. 154(b) by 1437 days.

(21) Appl. No.: 13/582,747

(22) PCT Filed: Mar. 17, 2011

(86) PCT No.: PCT/IL2011/000259
§ 371 (c)(1),
(2), (4) Date: Sep. 5, 2012

(87) PCT Pub. No.: WO2011/114333
PCT Pub. Date: Sep. 22, 2011

(65) Prior Publication Data
US 2013/0006124 A1  Jan. 3, 2013

Related U.S. Application Data

(60) Provisional application No. 61/314,611, filed on Mar. 17, 2010.

(51) Int. Cl.
*A61B 5/024* (2006.01)
*A61B 5/11* (2006.01)
(Continued)

(52) U.S. Cl.
CPC .......... *A61B 5/024* (2013.01); *A61B 5/02405* (2013.01); *A61B 5/4812* (2013.01);
(Continued)

(58) Field of Classification Search
None
See application file for complete search history.

(56) References Cited

U.S. PATENT DOCUMENTS 7,753,849 B2 * 7/2010 Morgan et al. ............... 600/453
8,083,682 B2 * 12/2011 Dalal .................. A61B 5/0205
600/483
(Continued)

FOREIGN PATENT DOCUMENTS

EP        2087841       8/2009
WO      WO0120036    *   3/2001   ............... C12Q 1/68
(Continued)

OTHER PUBLICATIONS

International Preliminary Report on Patentability dated Sep. 27, 2012 From the International Bureau of WIPO Re. Application No. PCT/IL2011/000259.
(Continued)

*Primary Examiner* — Jacqueline Cheng
*Assistant Examiner* — Jairo Portillo

(57) ABSTRACT

A method of analysis is disclosed. The method comprises receiving a non-ECG signal indicative of heart beats of a sleeping subject; extracting from the signal a series of inter-beat intervals (IBI); calculating at least one Poincare parameter characterizing a Poincare plot of the IBI series; and using the Poincare parameter(s) to determine a REM sleep of the sleeping subject. In some embodiments, sleep stages other than REM sleep and/or wake stages are determined.

21 Claims, 4 Drawing Sheets

(51) Int. Cl.
   *A61B 5/00* (2006.01)
   *A61B 7/00* (2006.01)
(52) U.S. Cl.
   CPC ............ *A61B 5/02416* (2013.01); *A61B 5/11* (2013.01); *A61B 5/4809* (2013.01); *A61B 5/726* (2013.01); *A61B 7/00* (2013.01)

(56) References Cited

U.S. PATENT DOCUMENTS

| | | | |
|---|---|---|---|
| 2005/0250745 A1* | 11/2005 | Seddon | A61K 31/555 514/165 |
| 2006/0178588 A1* | 8/2006 | Brody | 600/513 |
| 2006/0235315 A1* | 10/2006 | Akselrod et al. | 600/509 |
| 2007/0123787 A1* | 5/2007 | Kitajima | A61B 5/02416 600/509 |
| 2008/0287815 A1* | 11/2008 | Chon | A61B 5/0806 600/507 |
| 2010/0041079 A1* | 2/2010 | Yusuf | G01N 33/54366 435/7.92 |
| 2010/0274147 A1* | 10/2010 | Patangay et al. | 600/515 |
| 2011/0004110 A1* | 1/2011 | Shusterman | 600/509 |

FOREIGN PATENT DOCUMENTS

| | | |
|---|---|---|
| WO | WO 2004/026133 | 4/2004 |
| WO | WO 2008/132736 | 11/2008 |
| WO | WO 2011/114333 | 9/2011 |

OTHER PUBLICATIONS

Office Action dated Feb. 4, 2015 From the Israel Patent Office Re. Application No. 221822 and Its Translation Into English.
International Search Report and the Written Opinion dated Sep. 15, 2011 From the International Searching Authority Re. Application No. PCT/IL2011/000259.
Otzenberger et al. "Temporal Relationship Between Dynamic Heart Rate Variability and Electroencephalographic Activity During Sleep in Man", Neuroscience Letters, XP007912072, 229: 173-176, Jan. 1, 1997.
Raetz et al. "Dynamic Characteristics of Cardiac R-R Intervals During Sleep and Walking States", Sleep, XP009130390, 14(6): 526-533, Dec. 1, 1991.

* cited by examiner

SLEEP ANALYSIS BASED ON INTER BEAT INTERVAL

RELATED APPLICATION

This application is a National Phase of PCT Patent Application No. PCT/IL2011/000259 having International filing date of Mar. 17, 2011, which claims the benefit of priority under 35 USC § (e) of U.S. Provisional Patent Application No. 61/314,611, filed on Mar. 17, 2010, The contents of the above applications are all incorporated by reference as if fully set forth herein in their entirety.

FIELD AND BACKGROUND OF THE INVENTION

The present invention, in some embodiments thereof, relates to sleep analysis and, more particularly, but not exclusively, to sleep analysis based on inter beat interval.

In medicine, it takes a long period of observation to further understand the statuses of patients. Sleep medicine has made great progress in the past years, including apnea and some other chronic diseases related to sleep have been paid more attention to. Some medical research has also shown that sleep problems may be one of the causes of hypertension. The growing interest in sleep and its disorders, including their influence on health, well-being and public safety (such as in car accidents) has therefore caused a continuously increasing need to perform sleep investigations for both research and clinical purposes.

It is common to broadly divide the sleep of a normal healthy individual into three states: Wakefulness, Rapid-Eye-Movement (REM) sleep and Non-REM (NREM) sleep. NREM sleep is oftentimes further subdivided into three sleep stages, known as Stage-1, Stage-2 and Stage-3 according to the increasing threshold to the influence of external stimuli. These stages are also known as the depth of sleep. Stage 3 is sometime referred to as slow wave sleep (SWS) and Stages 1 and 2 are combined to define light sleep (LS).

Sleep stages have been traditionally monitored and examined clinically with a polysomnograph (PSG), which provides data regarding the electrical activity of brain, muscles and eye movement during sleep. The PSG data are analyzed according to a gold standard procedure attributed to Rechtschaffen and Kales (R&K) [Rechtschaffen A., Kales A., eds., "A manual of standardized terminology, techniques and scoring system for sleep staging in human subjects", Washington D.C.: US Government Printing Office, NIH Publication 204, 1968]. The R&K criteria are primarily based on the analysis of three collected bio-signals: (i) electroencephalogram (EEG), (ii) electrooculogram (EOG), and (iii) electromyogram (EMG). The standard procedure is as follows: EEG signals are derived primarily from the cortex of the brain. At the same time an EMG signal which monitors muscle activity, generally from one of the muscles of the mandible (submental) is measured, together with left eye and right eye EOG (signals produced by eyeball movements relative to the skull). These EEG, EMG and EOG signals are conventionally recorded on a multi-channel physiological recorder.

The number of physiologic inputs which are required in the PSG procedure may vary. Typically, the monitored signals include 2-4 EEG leads, 2 EOG leads, 1-3 or more EMG leads (chin, limbs), airflow monitoring, 1-2 respiratory effort leads, oxygen saturation monitoring, 3 electrocardiogram (ECG) leads, body position monitoring and a microphone. Data is stored during the sleep, and the analysis is typically done manually off-line, according to the standard R&K criteria.

U.S. Pat. No. 7,623,912 to Akselrod et al. describes a technique for determining sleep stages from an ECG signal. A series of cardiac R-R intervals is extracted from the ECG signal and decomposed by a time-frequency decomposition. The time-frequency decomposition is used for determine SWS period and sleep-onset period. EMG parameters are also extracted from the ECG signal and are used for determining REM period. Akselrod et al. also discloses a Poincare plot of the R-R intervals and describes technique for determining REM sleep based on the plot. The contents of Akselrod et al. is incorporated by reference as if fully set forth herein.

SUMMARY OF THE INVENTION

According to an aspect of some embodiments of the present invention there is provided a method of analysis. The method comprises: receiving a signal indicative of heart beats of a sleeping subject, the signal being other than an electrocardiogram (ECG) signal; extracting from the signal a series of inter-beat intervals (IBI); calculating at least one Poincare parameter characterizing a Poincare plot of the IBI series; and using the at least one Poincare parameter to determine a REM sleep of the sleeping subject.

According to some embodiments of the invention the signal is generated by converting a mechanical wave into an electrical signal. According to some embodiments of the invention the signal is generated by converting an optical wave into an electrical signal. According to some embodiments of the invention the signal is generated by converting an electromagnetic wave into an electrical signal.

According to some embodiments of the invention the signal is indicative of at least one of: a local blood pressure of the subject, a local blood volume of the subject, a cardiac sound, and skin displacements caused by pulsatile blood flow in the vasculature of the subject.

According to some embodiments of the invention the method comprises calculating balance between odd and even quantiles in the Poincare, wherein the REM sleep is determined based on the balance.

According to some embodiments of the invention the REM sleep is determined based on a number of points in a vicinity of an identity line of the Poincare plot.

According to some embodiments of the invention the method comprises calculating a plurality of moments with respect to a predetermined line along the Poincare plot, each of the plurality of moments being calculated within a predetermined time-window.

According to some embodiments of the invention the method comprises accessing an annotated library of parameters and searching for parameters similar to the calculated Poincare parameter(s) so as to determine the REM sleep.

According to some embodiments of the invention the method comprises obtaining a time-frequency decomposition of the IBI series and calculating at least one frequency parameter from the time-frequency decomposition, wherein the determining the REM sleep is based, at least in part, on the at least one frequency parameter.

According to some embodiments of the invention the method further comprises determining at least one sleep stage selected from the group consisting of light-sleep (LS) and slow wave sleep (SWS).

According to some embodiments of the invention the method comprises determining at least one sleep-onset.

According to some embodiments of the invention the method comprises determining at least one non-sleep period, selected from the group consisting of an awakening period and an arousal period.

According to an aspect of some embodiments of the present invention there is provided a computer software product, comprising a computer-readable medium in which program instructions are stored, which instructions, when read by a data processor, cause the data processor to receive a signal indicative of heart beats of a sleeping subject and execute at least a few of the operations of the method described herein.

According to an aspect of some embodiments of the present invention there is provided a system for analysis. The system comprises: a sensing device adapted for generating a signal indicative of heart beats of a sleeping subject the signal being other than an electrocardiogram (ECG) signal; and a data processor configured for receiving the signal, extracting from the signal a series of inter-beat intervals (IBI), constructing at least one Poincare parameter characterizing a Poincare plot of the IBI series, and determining a REM sleep of the sleeping subject responsively to the Poincare parameter.

According to some embodiments of the invention the sensing device is configured for converting a mechanical wave into an electrical signal. According to some embodiments of the invention the sensing device is configured for converting an optical wave into an electrical signal. According to some embodiments of the invention the sensing device is configured for converting an electromagnetic wave into an electrical signal.

According to some embodiments of the invention the sensing device is configured for sensing at least one of: a local blood pressure of the subject, a local blood volume of the subject, a cardiac sound, and skin displacements caused by pulsatile blood flow in the vasculature of the subject.

According to some embodiments of the invention the sensing device is selected from the group consisting of a plethysmograph, a microphone, a radar, an accelerometer and a displacement sensing device.

According to some embodiments of the invention the data processor is configured for calculating balance between odd and even quantiles in the Poincare, wherein the REM sleep is determined based on the balance. According to some embodiments of the invention the quantiles are quartiles.

According to some embodiments of the invention the REM sleep is determined based on a number of points in a vicinity of an identity line of the Poincare plot.

According to some embodiments of the invention the data processor is configured for calculating a plurality of moments with respect to a predetermined line along the Poincare plot, each of the plurality of moments being calculated within a predetermined time-window.

According to some embodiments of the invention the data processor is configured for accessing an annotated library of parameters and searching for parameters similar to the calculated Poincare parameter(s) so as to determine the REM sleep.

According to some embodiments of the invention the data processor is configured for obtaining a time-frequency decomposition of the IBI series and calculating at least one frequency parameter from the time-frequency decomposition, wherein the REM sleep is determined based, at least in part, on the frequency parameter(s).

According to some embodiments of the invention the data processor is configured for determining at least one sleep stage selected from the group consisting of light-sleep (LS) and slow wave sleep (SWS).

According to some embodiments of the invention the data processor is configured for determining at least one sleep-onset.

According to some embodiments of the invention the data processor is configured for determining at least one non-sleep period, selected from the group consisting of and awakening period and an arousal period.

According to some embodiments of the invention the frequency parameter(s) comprises at least one power spectrum component selected from the group consisting of a very-low-frequency (VLF) power spectrum corresponding to a frequency band defined from about 0.008 Hz to about 0.04 Hz, a low-frequency (LF) power spectrum corresponding to a frequency band defined from about 0.04 Hz to about 0.15 Hz, a high-frequency (HF) power spectrum corresponding to a frequency band defined from about 0.15 Hz to about 0.5 Hz, and any combination of at least two of the VLF power spectrum, the LF power spectrum and the HF power spectrum.

According to some embodiments of the invention at least one of the VLF, the LF and the HF power spectra are calculated within a time-window along the IBI series, the window having a width which is a function of a respective frequency.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a data processor or a computer, using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
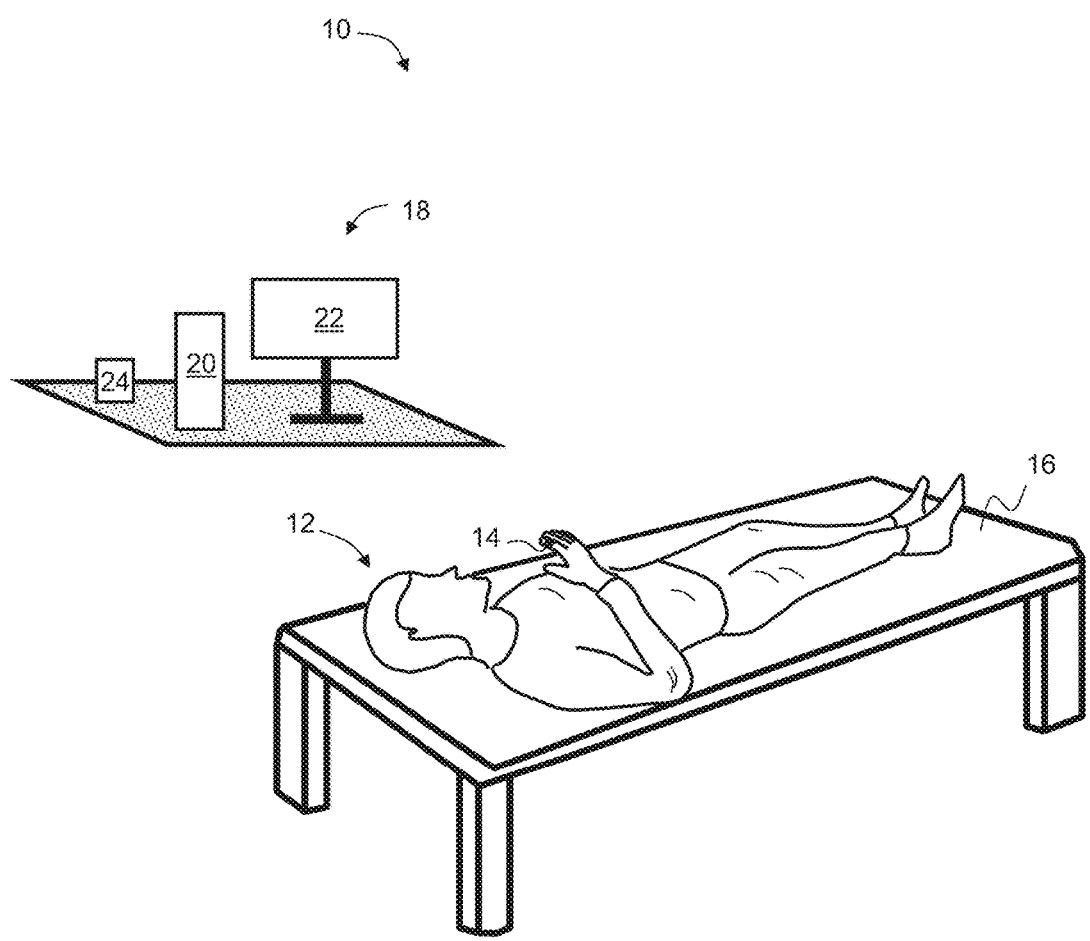
FIG. 1 is a schematic illustration of a system suitable for sleep monitoring and analysis, according to some embodiments of the present invention.

The present invention, in some embodiments thereof, relates to sleep analysis and, more particularly, but not exclusively, to sleep analysis based on inter beat interval.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

FIG. 1 is a schematic illustration of a system 10 suitable for sleep monitoring and analysis, according to some embodiments of the present invention.

System 10 is particularly useful used for monitoring a subject 12, preferably during sleep, at home, or in clinic or hospital ward environment, but may also be used in a dedicated sleep laboratory. System 10 receives and analyzes a signal from a suitable sensing device 14. Device 14 provides a signal indicative of heart beats of a sleeping subject. Preferably, device 14 provides a signal other than an ECG signal. For example, in various exemplary embodiments of the invention sensing device 14 converts mechanical, optical or electromagnetic waves into electrical signal. Representative of signals suitable for the present embodiments including, without limitation, blood pressure related signal, blood volume related signal, acoustic related signal (e.g., heart sound), displacement related signal, and the like. Device 14 can thus be of any type provided it generates a signal, preferably electrical signal, such as one of the above signals.

Depending on the type of signal, sensing device 14 may or may not be physically attached to the subject.

For example, in some embodiments of the present invention device 14 is a plethysmograph (e.g., photoplethysmograph) sensor which may be connected to one of the fingers on the hand of subject 12, as shown in FIG. 1, or elsewhere on the body of subject 12. In these embodiments, sensing device 14 provides a blood pressure or blood volume related signal.

In some embodiments of the present invention device 14 comprises a microphone which can be connected to a location on subject 12 such that the microphones generates an electrical signal in response to the sound of pulsatile blood flow in the subject's blood vessels or the sound of the heart itself, as known in the art. In these embodiments, sensing device 14 provides acoustic related signal.

In some embodiments of the present invention device 14 is a transducer/receiver device configured for detecting heart rate via radar technology. For example, the device can feature micro impulse radar pulses, wherein the distances between local maxima can be calculated and analyzed from the detected radar signal. Suitable transducer/receiver device is described in Florian Michahelles, Ramon Wicki, Bernt Schiele, "Less Contact: Heart-Rate Detection Without Even Touching the User," iswc, pp. 4-7, Eighth IEEE International Symposium on Wearable Computers (ISWC'04), 2004, the contents of which are hereby incorporated by reference. The radar can optionally and preferably be a Doppler radar, particularly, but not exclusively, a non-contact Doppler radar. Doppler radars suitable for the present embodiments are described in U.S. Pat. Nos. 4,513,748 and 7,753,849 and references therein, the contents of which are hereby incorporated by reference.

In some embodiments of the present invention device 14 is a displacement, motion or vibration sensor (e.g., acoustic sensing device) which is connected to the body of subject 12 or to structure 16 supporting subject 12 (e.g., under the mattress), and which is configured for sensing vibrations of the subject's skin (directly or via structure 16) that are caused by the pulsatile blood flow in the vasculature of the subject. In these embodiments, sensing device 14 provides displacement related or acoustic related signal. Alternatively, device 14 can be an accelerometer which also provides data indicative of skin motion caused by blood flow. Motion, displacement and vibration sensors of sufficient sensitivity for sensing changes with such small amplitudes are known in the art and found, for example, in International Publication Nos. WO 00/67013, WO 03/036321, WO 03/048688, WO 2004/072658, WO 2005/062719, and WO2005/076727, and U.S. Pat. Nos. 6,984,993 and 7,080,554.

Additional techniques for sensing signals indicative of heart beats suitable for use in system 10 are known in the art and described, for example, in Reisner et al. Anesthesiology 2008, 108:950; Tazawa et al., The Auk, 1991, 108:594; and Verkruysse Otpics express 2008, 16:No 26, the contents of which are hereby incorporated by reference.

It is expected that during the life of a patent maturing from this application many relevant technologies for detecting signals indicative of heart beats will be developed and the scope of the term signal indicative of heart beats is intended to include all such new technologies a priori.

In various exemplary embodiments of the invention system 10 performs the analysis based on a single channel of the signal. For example, system 10 may employ a single sensing device that provides the signal. Alternatively, system 10 can comprise more than one sensing device, and the sleep analysis is based on signal received from one of the sensing devices but not from any other of the sensing devices. In various exemplary embodiments of the invention system 10 performs the analysis without using a multiple lead ECG signal. In some embodiments, system 10 performs the analysis without determining the morphology of an ECG signal. In some embodiments, system 10 performs the analysis without using ECG signal.

System 10 can comprise a data processor 20 that processes and analyzes the signals from sensing device 14 using the technique described hereinbelow.

The term "data processor" as used herein, includes any suitable device for processing data, including, without limitation, a microcomputer, a microprocessor, and a data processing system. A data processor can be electronic computing circuitry (e.g., a central processing unit) or a system associated with such circuitry. Representative examples include, without limitation, a desktop home computer, a workstation, a laptop computer and a notebook computer. Also contemplated is a dedicated system having electronic computing circuitry therein. Optionally, such a dedicated system is portable. Optionally, such a dedicated system is hand held or wearable, e.g., on the arm of the user. Also contemplated are systems which are capable of receiving and processing data but may also have other functions. Representative examples include, without limitation, a cellular telephone with data processing functionality, a personal digital assistant (PDA) with data processing functionality, a portable email device with data processing functionality (e.g., a BlackBerry® device), a portable media player with data processing functionality (e.g., an Apple iPod®), a portable gaming device with data processing functionality (e.g., a Gameboy®), and a tablet or touch screen display device with data processing functionality (e.g., an Apple iPad®).

Data processor can receive the data from sensing device 14 using a wired communication line or via wireless communication (e.g., Bluetooth® communication, WiFi® communication, Infrared Data Association communication, home radio frequency communication etc.).

Data processor 20 may optionally and preferably be coupled, e.g., via a network receiver/transmitter 24 to communicate over a network, such as a telephone network or the Internet, with a remote data processor (not shown). This configuration allows performing the sleep study while subject 12 is at a remote location (e.g., at home), and also allows performing simultaneous sleep studies in multiple different locations. Processor 20 can be a general-purpose processor (which may be embedded in a bedside, remote monitor or a dedicated system) with suitable software for carrying out the functions described below. This software may be downloaded to processor 20 in electronic form, or it may alternatively be provided on tangible media, such as optical, magnetic or non-volatile electronic memory. Alternatively, processor 20 can includes a dedicated circuitry constituted for carrying out the functions described below.

Processor 20 processes the signals in order to identify one or more sleep stages. Optionally, the processor accesses a library of parameters during the processing. An example of a library which includes a dataset for characterizing sleep parameters is described in U.S. Pat. No. 7,623,912, the contents of which are hereby incorporated by reference. Data processor 20 can be a part of a console 18, which may include a display device 22. The results of the analysis can be used for issuing a report which is optionally and preferably displayed on a display device 22, such as, but not limited to, a computer monitor or the like, to present the results of the analysis to an operator, such as a physician. Alternatively or additionally, data processor 20 may also be provided with an embedded display in which case the results can be displayed on the embedded display. The results can also be transmitted to a computer readable medium for storage. Also contemplated are embodiments in which the results of the analysis are transmitted to a remote location where the results can be displayed and/or stored as desired.

Figure 2:
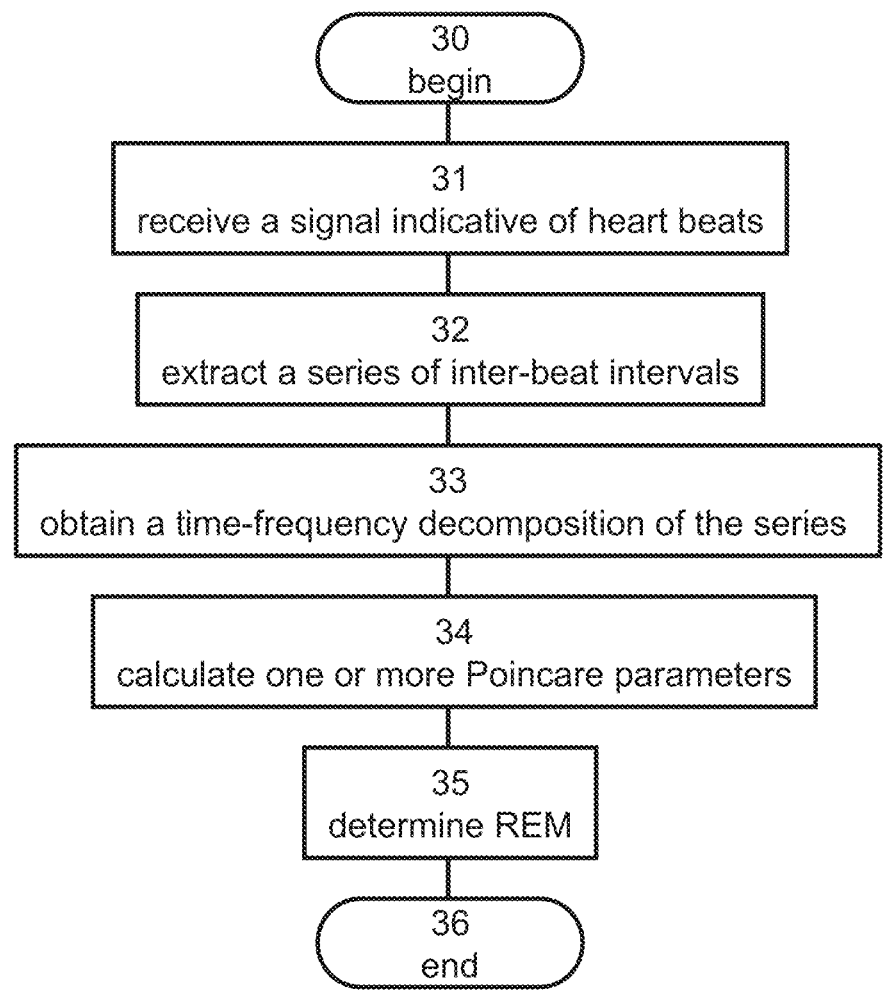
FIG. 2 is a flowchart diagram of a method suitable for analysis, in embodiments of the invention in which the analysis is used at least for determining REM sleep.
Figure 3:
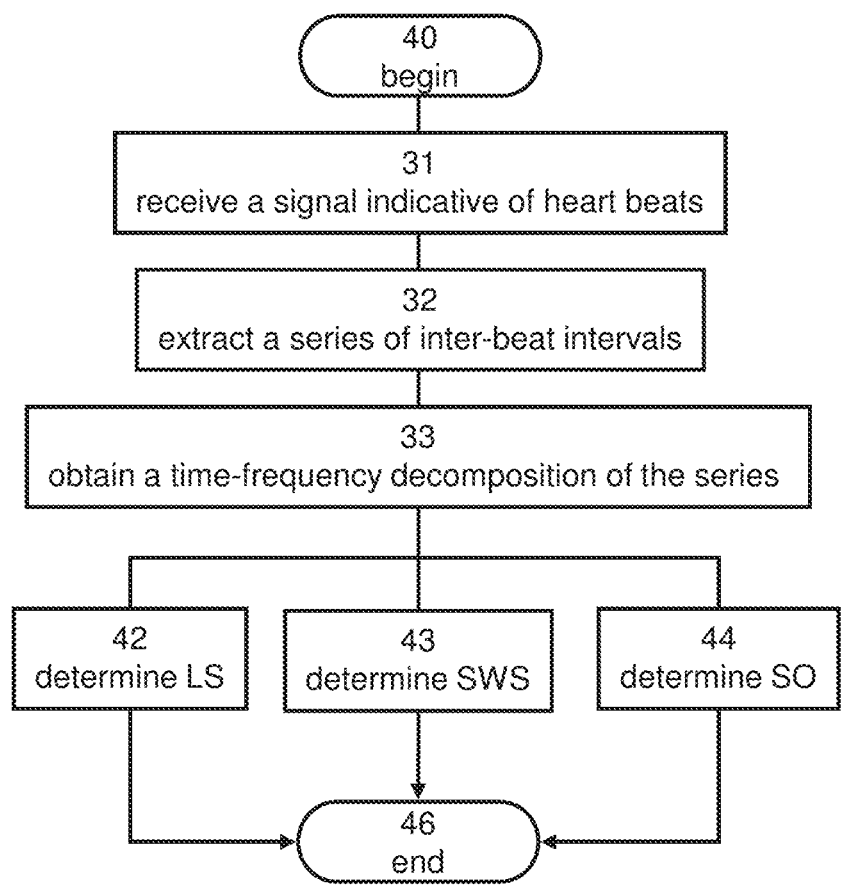
FIG. 3 is a flowchart diagram of a method suitable for analysis, in embodiments of the invention in which the analysis is used at least for determining one or more sleep stages other than REM.

Reference is now made to FIGS. 2 and 3 which are flowchart diagrams of a method suitable for analysis according to various exemplary embodiments of the present invention.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

At least part of the operations described below can be implemented by a data processing system, e.g., a dedicated circuitry or a general purpose computer (e.g., processor 20), configured for receiving the data and executing the operations described below. A representative and non-limiting example of a data processing system suitable for the present embodiments is described hereinunder with reference to the block diagram of FIG. 4.

Computer programs implementing the method of the present embodiments can commonly be distributed to users on a distribution medium such as, but not limited to, a floppy disk, a CD-ROM, a flash memory device and a portable hard drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The method of the present embodiments can be embodied in many forms. For example, it can be embodied in on a tangible medium such as a computer for performing the method operations. It can be embodied on a computer readable medium, comprising computer readable instructions for carrying out the method operations. It can also be embodied in electronic device having digital computer capabilities arranged to run the computer program on the tangible medium or execute the instruction on a computer readable medium.

FIG. 2 is a flowchart diagram of a method suitable for analysis, in embodiments of the invention in which the analysis is used at least for determining REM sleep.

The method begins at 30 and continues to 31 at which a signal indicative of heart beats of a subject, such as subject 12 (see FIG. 1) is received. The subject is preferably sleeping. The signal can be of any of the aforementioned types, and it can be input directly from a suitable sensing device (e.g., sensing device 14), or, following some pre-processing such as filtration, digitization and the like.

The method continues to 32 at which a series of inter-beat intervals (IBI) are extracted from the signal. In various exemplary embodiments of the invention the series of IBI is extracted from a single channel of the signal.

As used herein IBI refers to the duration of a heart beat on a beat by beat basis. The IBI is inversely proportional to the heart rate (HR).

The IBI can be extracted directly from the signal, for example, by identifying peaks in the signal and determining the duration between successive peaks. In some embodiments of the present invention the IBI is based on beat by beat values without any averaging. The advantage of this embodiment is that it allows identification of variability within the series. Thus, in this embodiment, the time resolution at which the IBI is extracted is preferably sufficiently high to reflect the beat-to-beat variability. In some embodiments of the present invention a 200 Hz resolution is employed. It is recognized that higher time resolutions correspond to signal of higher quality. Nevertheless, the present inventors discovered a correction procedure that can be employed for handling missing beats in the IBI signal. The correction procedure generally includes interpolation in order to close data time-gaps which are sufficiently short (e.g., time-gaps spanning over about 5 heart beats or less). When the data include longer time-gaps, the analysis can be performed in segmentation. The IBI series is optionally and preferably used for excluding spurious points from the data.

In some embodiments of the present invention the method continues to 33 at which a time-frequency decomposition of the IBI series is obtained. The time-frequency decomposition may be obtained in any way known in the art for calculating the frequency content of a series. According to some embodiment of the present invention, the time-frequency decomposition is obtained by calculating at least one time-dependent power spectrum component. The power spectrum components include, but are not limited to, a very-low-frequency (VLF) power spectrum, a low-frequency (LF) power spectrum and a high-frequency (HF) power spectrum. A more detailed description of a procedure of obtaining the time-frequency decomposition is provided hereinunder.

As a general rule, the frequency bands reflect different activities of the autonomic nervous system. Specifically, high-frequencies reflect the fast reacting parasympathetic activity while low- and very-low-frequencies reflect both the parasympathetic and the slow reacting sympathetic activities.

The VLF power spectrum is typically defined for frequencies of from about 0.008 Hz to about 0.04 Hz, the LF power spectrum is typically defined for frequencies of from about 0.04 Hz to about 0.15 Hz, and the HF power spectrum is typically defined for frequencies of from about 0.15 Hz to about 0.5 Hz. According to some embodiments of the present invention, a combination of two or more of the above spectra is also calculated. For example, one power parameter may be the ratio LF/HF, and another power parameter may be the ratio VLF/HF. The ratio LF/HF is also known as the sympathovagal balance.

The method optionally and preferably continues to 34 at which one or more Poincare parameters are calculated from the IBI series. A Poincare parameter is a parameter that characterizes, at least partially, a Poincare plot. A Poincare plot is a graph generated from a vector of data. Typically, a Poincare plot is a two-dimensional graph in which a particular point on the graph represents a dependence of one datum of the vector on a preceding datum of the same vector, where the latter datum (the preceding) may be referred to as "the cause" and the former datum may be referred to as "the effect". In other words, the Poincare plot represents the dependence of a data set on its history. The gap between "the cause" and "the effect" may vary. According to some embodiments of the present invention, the gap is from about one heart-beat to about 10 heart-beats or more.

Although the Poincare parameters characterize a Poincare plot, it is not necessary to construct the plot in order for a particular Poincare parameter to be calculated. This is because some Poincare parameters can be calculated directly from the relation between elements of the IBI series, and some Poincare parameters are calculated while the plot is being constructed. Nevertheless, the construction of a Poincare plot before, during or after the calculation of one or more Poincare parameter is not excluded from the scope of the present invention.

Unless otherwise defined, the use of the term "plot" is not to be considered as limited to the transformation of data into visible signals. For example, a plot, such as a Poincare plot can be stored as binary data (e.g., as a set of tuples) in a computer memory or any other computer-readable medium. Yet, in some embodiments of the present invention a plot can be transmitted to a display device such as a computer monitor, or a printer.

The method continues to 35 at which the Poincare plot is used for determining a REM sleep. This can be done in more than one way. In some embodiments of the present invention the method calculates the balance between odd and even quantiles (e.g., quartiles) in the Poincare plot, wherein the REM sleep is determined based on that balance. For example, when the balance is above a predetermined threshold the method determines that the subject is in REM sleep state, and otherwise the method determines that the subject is not in a REM sleep state. Alternatively, or additionally, the method can access an annotated library of data which comprises annotated values of such balance. In these embodiments, the method compares the calculated balance with the annotated balance values in the library until a matching balance is found, and determines whether or not the subject is in a REM sleep state based on the annotation associated with that balance.

The balance between odd and even quantiles is preferably calculated for a moving window in time in order to incorporate the variability of the balance during the time. A typical width of the window is, without limitation, about 60 seconds.

In some embodiments of the present invention the REM is determined based on a number of points in a vicinity of an identity line of Poincare plot. An identity line is a line defining all points for which the history datum is the same as the current datum. Typically, when the Poincare plot is visualized, such a line forms a 45° angle with the axes of the plot. The number of points in the vicinity of the identity line can be determine by defining on the plot a window of a predetermined width, associating the window with the identity line and counting the number of points falling in that window. A typical predetermined width of the window can be the time period spanned by a few (e.g., 2-5) sampling point. Thus, for example, when the absolute difference between two points is approximately the same or less than the time period spanned by a few sampling points the method can determine that both points are in the vicinity of the identity line.

The determination of REM sleep according to some embodiments of the present invention can be based on a thresholding procedure, wherein when the number of points in a vicinity of the identity line is above a predetermined threshold the method determines that the subject is in REM sleep state, and otherwise the method determines that the subject is not in a REM sleep state. Alternatively, or additionally, the method can access an annotated library of data which comprises annotated numbers of points in the vicinity of the identity line. In these embodiments, the method compares the counted number with the annotated number in the library until a matching number is found, and determines whether or not the subject is in a REM sleep state based on the annotation associated with that number.

The number of points in vicinity of the identity line is preferably calculated for a moving window in time in order to incorporate the variability of the parameter during the time. A typical width of the window is, without limitation, about 60 seconds.

The present embodiments also contemplate other Poincare parameters. In some embodiments of the present invention the Poincare parameters include one or more moments calculated for points of the Poincare plot which are selected within a predetermined time-widow (e.g., a two-minute time-window, a three-minute time-window, etc.).

Many moments are contemplated. One such moment is a moment of inertia. Broadly speaking, the moment of inertia is calculated by performing a summation of a plurality of squared distances of a plurality of points from a point, a line or a plane of reference, where each term in the summation is weighted by a respective mass. In one embodiment, all the points on the Poincare plot have equal "masses". Hence, the moment of inertia is defined by $IM=m\Sigma D_i^2$, where $D_i$ is a distance of the ith point of the Poincare plot from a predetermined line along the plot, m is an arbitrary mass parameter and the summation is over at least a portion of the points. The predetermined line is typically a straight line, such as, but not limited to, the aforementioned identity line.

Irrespective of the type of moments being chosen, the calculated moments may be normalized by dividing each moment by the total number of points. In addition, some of the points of the Poincare plot, failing to obey some statistical requirement, may be excluded from the calculation. For example, in embodiments in which the moments of inertia are used the statistical requirement may be that the distance, D, is smaller than the average of absolute D plus one standard deviation of D.

When the Poincare parameters include moments, the REM sleep can be identified when the respective moment which is below a predetermined threshold.

In some embodiments of the present invention the method uses one or more of the power spectra or frequency parameters as calculated from the time-frequency decomposition for determining the REM sleep. This can be done, for example, by accessing an annotated library of data which comprises annotated frequency parameters. In these embodiments the method compares the calculated frequency parameters with the annotated frequency parameters in the library until a matching parameter or set of parameters is found, and determines whether or not the subject is in a REM sleep state based on the annotation associated with that parameter or set of parameters.

Once the REM sleep is determined a report regarding the analysis can be issued, for example, by displaying the results on a display device and/or transmit them to computer readable medium. Optionally, the results can be transmitted over a network to a remote location at which they can be displayed and/or stored. The results of the analysis are optionally and preferably clustered over the time axis into a plurality of segments, each corresponding to one epoch of sleep. Thus, a cluster of instants at which REM sleep has been identified can be reported as an epoch at which the subject is in REM sleep, and a cluster of instants at which no REM sleep has been identified can be reported as an epoch at which the subject is not in REM sleep. A typical duration of an epoch is from about 10 seconds to about 60 seconds. Other durations are not excluded from the scope of the present invention.

The method ends at 36.

FIG. 3 is a flowchart diagram of a method suitable for analysis, in embodiments of the invention in which the analysis is used at least for determining one or more sleep stages other than REM.

The method begins at 40 and continues to 31 at which a signal indicative of heart beats of a subject is received as further detailed hereinabove. The method continues to 32 at which a series of IBI is extracted from the signal as further detailed hereinabove.

The method optionally and preferably continues to 33 at which a time-frequency decomposition of the IBI series is obtained, as further detailed hereinabove. The method then proceeds to at least one of 42, 43 at which the method uses one or more of the power spectra or frequency parameters as calculated from the time-frequency decomposition for determining a non-REM (NREM) sleep stage, such as, but not limited to, light-sleep (LS) and slow wave sleep (SWS). Optionally and preferably the method continues to 44 at which sleep-onset (SO) is determined.

The determination of LS, SWS and/or SO can be by a thresholding procedure or it can be based on a search in a library database. Also contemplated is a combination of the two approaches in which case an appropriate weight can be given to each approach.

SO is commonly referred to as a transition between quiet wakefulness and sleep. When a thresholding procedure is employed for determining SO, epochs corresponding to SO are preferably defined as being characterized by one or more SO parameters which is above a predetermined threshold, over a predetermined time range (typically 2-10 epochs). As the SO parameter(s) can be calculated by integrating one or more of the aforementioned power spectra over predetermined frequency limits. In some embodiments, the SO parameters are defined as time-dependent power ratios calculated using the integrated power spectra. The time-dependent power ratios may be, for example, a ratio between two integrated power spectra or a ratio between an integrated power spectrum and an integrated total power.

Beside integration limits which are the frequency thresholds defining the various power spectrum components, other integration limits may be used so as to optimize the ability of the SO parameters to characterize transition between quiet wakefulness and sleep.

One procedure for calculating the integration limits, according to some embodiments of the present invention, is by obtaining a steady state power spectrum from the IBI series and employing a minimum-cross-entropy method so as to separate between frequency peaks of the steady state power spectrum. The steady state power spectrum may be obtained by any known mathematical transform such as, but not limited to, a Fourier transform. The minimum-cross-entropy method is found, e.g., in the following publications, the contents of all of which are hereby incorporated by reference: Kullback, S., "Information Theory and Statistics", John Wiley, New York, 1959; Seth, A. K., Kapur J. N., "A comparative assessment of entropic and non-entropic methods of estimation", *Maximum Entropy and Bayesian Methods*, Fougere, P. F. (Ed.), Kluwer Academic Publishers, 451-462, 1990; Brink, A. D., Pendock N. E., "Minimum Cross-Entropy Threshold Selection", *Patt. Recog.* 29:179-188, 1996. The advantage of using the minimum-cross-entropy threshold method is that this method, without assuming any a priori knowledge about the original spectrum distribution, sets the optimal integration limits so that the difference in the information content between the original and segmented spectra is minimized.

In some embodiments of the present invention the SO parameter is normalized and/or analyzed by calculating a plurality of statistical quantities, such as, but not limited to, an average, a variance and a t-test.

When the determination of SWS is by thresholding, a predetermined threshold is optionally and preferably selected for separating SWS periods from NSWS periods. An epoch of SWS can be defined, for example, when a calculated power parameter is below a predetermined threshold. For example, a constant threshold may be imposed on the value of the LF power and/or the VLF power. A typical numerical value for this threshold is below the median (e.g., at about one third) of the possible range of the LF and/or VLF powers. Also contemplated, is a threshold which varies from one sleeping subject to another. For example, a power parameter may be averaged over the entire sleep of the sleeping subject. This average power parameter, which can be considered as a particular power average for the sleeping subject, may be used for choosing the threshold. For example, suppose that the power parameter is a ratio between LF power and HF power. Then, denoting the average of LF/HF for the entire sleep of the sleeping subject by (LF/HF), the predetermined threshold is a function of (LF/HF). The threshold may be a linear function of (LF/HF) where the parameters of linear function are determined from experimental measurements.

Optionally the threshold(s) also vary with time. In this embodiment, the numerical values of the above threshold is adapted to the overall tendency of power balance to change over the sleep. For example, if a constant threshold is used, this constant threshold is selected to be smaller during the beginning of the sleep and higher towards the end of the sleep. If the threshold is a function of some average power parameter (e.g., (LF/HF)), the parameters of the function are selected so that the value of the function is smaller during the beginning of the sleep and higher towards the end of the sleep.

A similar approach can be employed also for other sleep stages, e.g., LS. Alternatively, a combined procedure, which includes both the determination of REM sleep (e.g., by following the operations described above with respect to FIG. 2) and the determination of other sleep stages can be employed. For example, an epoch can be defined as corresponding to LS if it is an NSWS epoch other than a REM epoch and other than a SO epoch. Preferably, epochs corresponding to a non-sleep state are also excluded from being identified as being LS epochs.

Broadly speaking, non-sleep periods are accompanied first by an acceleration of the heart-rate (i.e., a decrement of the IBI values) and second by a deceleration of the heart-rate (i.e., an increment of the IBI values), where the IBI decrement is slower than its increment. In addition, before a non-sleep period the IBI values are typically above the IBI mean value. In various exemplary embodiments of the invention these characteristics are used for the purpose of determining the epochs of non-sleep periods from the IBI series.

There are different types of non-sleep periods occurring during sleep, which, according to a preferred embodiment of the present invention, can be determined by the method of the present embodiments. These include, but are not limited to, awakening periods and arousal periods. For a detailed definition of awakenings and arousals during sleep the reader is referred to an article by Bonnet M. et al., entitled "EEG arousals: scoring rules and examples: a preliminary report from the Sleep Disorders Atlas Task Force of the American Sleep Disorders Association", published in *Sleep*, 15(2):173-84, 1992.

The main difference between awakenings and arousals is at the scale at which these non-sleep periods affect the ECG signal. Specifically the awakening periods, which are typically characterized by trace duration of at least 30 seconds, affect the low frequencies region while the arousals periods, which are typically characterized by trace duration of 5-10 seconds, affect the intermediate-high frequencies region.

Thus, according to some embodiments of the present invention, the IBI series is filtered using a low-pass-filter thereby providing a first series of signals. Then, the awakening periods are defined as a plurality of epochs each associated with at least one of the first series of signals which is below a predetermined threshold.

Similarly, for the purpose of determining the arousal periods, the IBI series is optionally and preferably filtered using a band-pass-filter thereby providing a second series of signals. Then, the arousal periods are defined as a plurality of epochs each associated with at least one of the second series of signals which is below a predetermined threshold.

Typical thresholds for the awakening and arousals periods are about 0.85 of the averaged value of the first series and the second series of signals, respectively. A typical cutoff frequency for the low-pass-filter is about 0.01 Hz, and typical cutoff frequencies of the band-pass-filter are 0.05 Hz for the low limit and about 0.2 Hz for upper band limit.

The method ends at 46.

Figure 4:
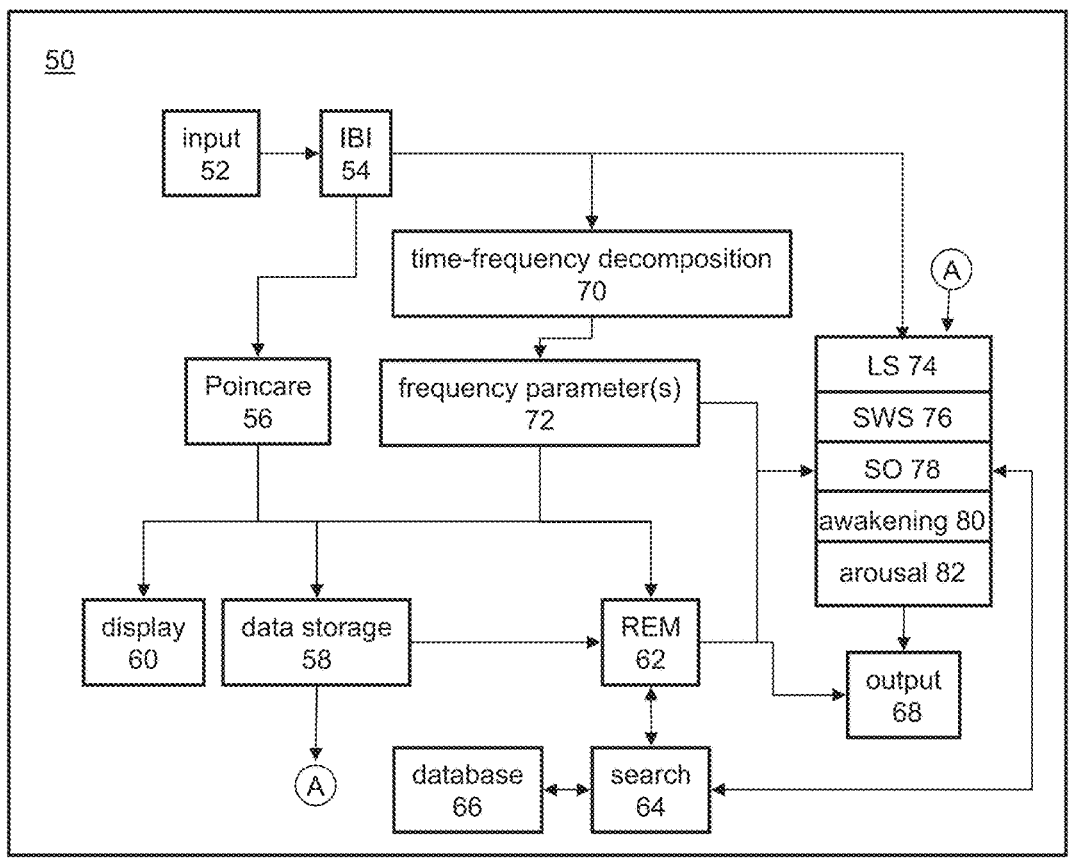
FIG. 4 is a block diagram describing a data processing system according to some embodiments of the present invention.

FIG. 4 is a block diagram describing a data processing system 50 suitable for executing various operations of the method described above. Data processing system 50 comprises a plurality of modules, each can be implemented as a dedicated circuitry within processor 20 of system 10 (see FIG. 1). Also contemplated, are embodiments in which one or more of the modules of data processing system 50 are tangibly embodied in a computer readable medium as computer program instructions, from which they can be loaded into the memory of a computer (e.g., a general purpose computer) for carrying out the respective operations. Further contemplated are embodiments in which some modules of system 50 are implemented as dedicated circuitry and some are embodied in a computer readable medium as computer program instructions.

System 50 comprises an input module 52 for receiving a signal indicative of heart beats of a sleeping subject. Input module 52 can be for example, for an A/D card when the signal is received directly from the sensing device, or an input data port such as a receptacle for a cable with a standard plug, such as a USB cable, or a dedicated plug, when the signal is a digital data stream. Input module 52 can also feature a wireless receiver in which case data is transmitted to input module using point to point wireless communication or broadcasted over a wireless communication network as known in the art. System 50 further comprises an IBI module 54 which receives the signal from input module 52 and extracts from a single channel of the signal a series of IBI, as further detailed hereinabove.

Optionally and preferably system 50 comprises a Poincare module 56 which calculates one or more Poincare parameters from the IBI series. Poincare module 56 optionally communicates with a data storage medium 58, which can be a computer memory or any other data writing device configured for writing data into a computer-readable medium. In some embodiments module 56 communicates with a display device 60 such as a computer monitor or a printer. In various exemplary embodiments of the invention system 50 comprises a REM module 62 which receives the Poincare parameter(s) from module 56 or medium 58 and determines the REM sleep of the subject based on the parameter(s), as further detailed hereinabove. REM module 62 is configured for extracting one or more of the aforementioned parameters from the Poincare plot. REM module 62 optionally and preferably communicates with a search module 64 which accesses a database 66 and searches it for matching parameters as further detailed hereinabove. The epochs identified as corresponding to REM sleep can be transmitted to an output module 68 which can be a display device and/or a receptacle for a cable with a standard or dedicated plug and/or a transmitter for wireless communication. Via output module 68, the identified epochs can also be stored in a computer readable medium.

In some embodiments of the present invention system 50 comprises a time-frequency decomposition module 70 which calculates a time-frequency decomposition of the IBI series as delineated hereinabove. A representative example of a procedure suitable for calculates a time-frequency decomposition is provided hereinunder. System 50 optionally and preferably comprises a frequency parameter module 72 which receive the time-frequency decomposition from module 70 and uses it for calculating one or more frequency parameters. Module 72 can also communicate with data storage module 58 for storing the calculated parameters, if desired. Optionally REM module 62 communicates with frequency parameter module 72 so as to allow determination of REM sleep based on the calculated frequency parameters. In various exemplary embodiments of the invention system 50 comprises at least one of a LS module 74, a SWS module 76, a sleep onset module 78, awakening module 80 and an arousal module 82. Modules 74, 76, 78, 80 and 82 receive the frequency parameters from module 72 and optionally also data from REM module 62 and determine LS, SWS, sleep onset, awakenings and/or arousals as further detailed hereinabove. Modules 74, 76, 78, 80 and 82 can also receive data (e.g., the frequency parameters) from data storage module 58. For clarity of presentation, data flow from storage module 58 to modules 74, 76, 78, 80 and 82 is shown via a block-diagram connector designated "A". In some embodiments of the present invention one or more of modules 74, 76, 78, 80 and 82 communicates with search module 64 for the purpose of determining the respective state by comparison to entries in database 66. Epochs identified by one or more of modules 74, 76, 78, 80 and 82 as corresponding to the respective sleep can be transmitted to output module 68. Via output module 68, the identified epochs can be displayed, transmitted to a remote location and/or stored in a computer readable medium.

A detailed description of a method of obtaining the time-frequency decomposition, according to a preferred embodiment of the present invention, is now provided. The method, referred to herein as Selective Discrete Algorithm (SDA), was developed by Keselbrener L. and Akselrod S. and is found, e.g., in U.S. Pat. No. 5,797,840 and in an article entitled "Selective discrete Fourier transform algorithm for time-frequency analysis: Methods and application on simulated and cardiovascular signals" published in *IEEE Trans. Biomed. Eng.*, 43:789, 1996, both of which are hereby incorporated by reference.

The SDA is a variable window method for time-dependent spectral analysis. This algorithm has been extensively validated on physiological signals (e.g., physiological signals in humans modulated by the ANS) under a variety of transient conditions. Generally speaking, the power spectrum of physiological signals in humans modulated by the ANS can be divided into the VLF range (below 0.04 Hz), the LF range (from 0.04 Hz to 0.15 Hz) and the HF range (above 0.15 Hz displaying a peak at about 0.2 Hz for adults and a peak at about 0.4 Hz for children). The HF range is mediated by the fast reacting parasympathetic nervous system, the LF range is mediated by both the parasympathetic nervous system and the slower reacting sympathetic nervous system and the VLF range is mediated by thermoregulation and unknown systems.

The SDA is directed at determining the power content of frequencies of interest embedded in the physiological signal. The essence of the SDA derives from a basic rule according to which the amount of information which is required to estimate the power of fluctuations is a decreasing function of the frequency of interest. More specifically, in order to estimate the power of a high frequency fluctuation, only a short string of data is required, while a low frequency fluctuation demands a much wider time window.

Hence, according to a preferred embodiment of the present invention, a selective windowed time-frequency (t-f) analysis is performed for providing the time-dependent power spectrum of the RRI series. For each time of interest and for each frequency of interest, a minimal time-window is chosen over the relevant digitized signal, as further detailed hereinbelow. According to a preferred embodiment of the present invention, a series of windows are generated along the signal within which the power spectrum of the frequencies under investigation is to be analyzed. Then, the power spectrum for a particular frequency within each window is determined.

According to a preferred embodiment of the present invention, the duration of the windows is generally a decreasing function of the frequency under investigation, preferably inversely proportional to the frequency. Hence, low frequencies are investigated using long time windows while high frequencies are investigated using short time windows. The t-f analysis can be at a wide range of resolutions, both in frequency and in time. Typically, the frequency resolution is in the order of 0.005 Hz at the low frequency end of the spectrum, with time resolution in the order of one minute. For the higher frequency end, frequency resolution is in the order of 0.02 Hz with time resolution of a few seconds. The time and frequency resolutions preferably reach intermediate values around the center of the t-f plane.

The selective windowed t-f analysis may be implemented by more than one way, for example, in one embodiment a wavelet transform is used, in another embodiment a selective discrete spectral transform is used, and the like.

In the embodiment in which wavelet transform is used, the aperture, duration and the time resolution between consecutive windows are defined by a prototype function h(t), a scale parameter, a, and a shift parameter, b, according to the wavelet transform $\int h_{ab}(t) f(t) \, dt$. Further information on wavelet processing, is found in an article by Daubaechies I., entitled "The Wavelet Transform, Time Frequency Localization and Signal Analysis", published in *IEEE Transactions on Information Theory*, Vol. 36. No. 5, 1990 the contents of which are hereby incorporated by reference.

As well known in the art, for a large scale parameter value, the prototype function is stretched such that the prototype wavelet acts as a low frequency function while, for a small scale parameter value, the prototype function is contracted such that the wavelet function acts a high frequency function. Hence, depending on the value assigned to scaling parameter, a, the wavelet function dilates or contracts in time, causing the corresponding contraction or dilation in the frequency domain. Thus, the wavelet transform provides a flexible time-frequency resolution and analyzes higher frequencies with better time resolution but poorer frequency resolution than lower frequencies.

In the embodiment in which a selective discrete spectral transform is used, a predetermined number of data points are selected from the windows. Based on the data points, the power spectrum of the frequency within the windows is calculated, using a mathematical transform, which may be, for example, a Fourier transform, a Haar transform, a Hartley transform, a sine transform, a cosine transform, a Hadamard transform, and the like. According to a preferred embodiment of the present invention the data points are selected by employing a low pass filter and undersampling technique such as moving average. Typically, the same number of data points is provided, irrespective of the duration of the windows, so as not to generate artifacts or normalization problems.

As mentioned hereinabove, the duration of windows is preferably inversely related to the frequency under investigation. Depending on the type of the selective windowed t-f analysis which is used, the duration of windows typically lies from about 2 periods to about 10 periods of the frequency under investigation. The windows can have different apertures including, but not limited to, a rectangular aperture, a Hanmming aperture, a Hanning aperture, a Blackman aperture, a Gaussian window, a Lorentzian window, a sinc window, any power of a sine window, any power of a cosine window, any derivative of these windows, and the like.

Some corrections may be employed to the obtained power spectra, depending on the combination of the type of transform and the aperture of the window. For example, if the Fourier transform is used with a rectangular window, then, to ensure the highest possible frequency resolution by minimizing side lobes, the obtained power spectra are preferably corrected by dividing by the corresponding sinc function.

The calculated power spectra may be represented for example, in a 3D form, a 2D contour map form and the like. For example, if a power spectrum is represented by a 3D time dependent power spectrum graph, a first axis of the graph may represent frequencies, a second axis may represent time and a third axis may represent the power spectrum. Irrespective of the selected representation, the t-f resolution is substantially inhomogeneous, so that an optimal time-resolution is achieved for each frequency. Specifically, low frequencies have high frequency resolution and reduced time resolution, while high frequencies have lesser frequency and better time resolution.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Figure 5:
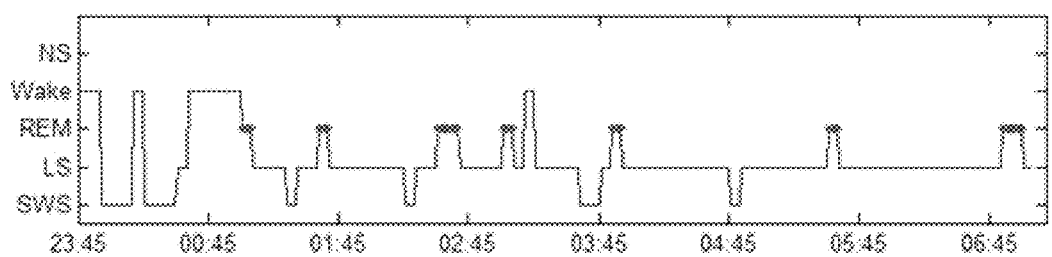
FIG. 5 shows information obtained according to some embodiments of the present invention from a whole night recording of an inter beat interval signal.

A male subject, age 30 years, height 186 cm, weight 75 Kg (BMI 21.7 Kg/m$^2$) was subjected to a full night (440 minutes) sleep monitoring. The subject was connected to a Pulse Oximetry sensor (Nonin Medical Inc., Plymouth, Minn.). The IBI signal was obtained from the photoplethysmograph signal generated by the Pulse Oximetry sensor. The IBI signal was processed and analyzed for determining various sleep and wake stages as described above with reference to FIGS. 1-4. Sleep onset was found to be 11 minutes from the beginning of the recording. The various sleep stages of the subject, as determined by the algorithm are visualized in FIG. 5 and summarized in Table 1, below.

TABLE 1

|  | Wake | Deep Sleep | Light Sleep | REM sleep | Total |
|---|---|---|---|---|---|
| Duration (Min) | 45 | 55 | 295 | 45 | 440 |
| Duration (%) | 10 | 13 | 67 | 10 | 100 |

TABLE 1-continued

|  | Wake | Deep Sleep | Light Sleep | REM sleep | Total |
|---|---|---|---|---|---|
| Arousals | N/A | 26 | 116 | 25 | 167 |
| Mean HR | 70 | 68 | 65 | 70 | 67 |
| Min HR | 30 | 33 | 31 | 49 | 30 |
| Max HR | 109 | 103 | 108 | 109 | 109 |

The above example demonstrates the ability of the method and system of the present embodiments to analyze non-ECG signals indicative of heart beat so as to determine one or more sleep stages or wake stages.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of determine a REM sleep of the sleeping subject, the method comprising:
   over a communication network, receiving from a sensing device having a circuit a signal indicative of heart beats of the sleeping subject, and storing said signal in a computer readable memory said signal being other than an electrocardiogram (ECG) signal, said receiving is by electronic computing circuitry remote from said sensing device;
   operating said electronic computing circuitry for:
   extracting from said signal a series of inter-beat intervals (IBI), constructing a Poincare plot of said IBI series and storing said Poincare plot in a computer readable memory;
   calculating, for a moving window in time, balance between odd and even quantiles in said Poincare plot wherein said quantiles are quartiles; and
   determining a REM sleep of the sleeping subject based on said balance; and
   transmitting information pertaining to said REM sleep over said communication network to a display being local with respect to said sensing device.

2. The method according to claim 1, wherein said signal is generated by converting a wave selected from the group consisting of a mechanical wave, an optical wave and an electromagnetic wave into an electrical signal.

3. The method according to claim 1, wherein said signal is indicative of at least one of: a local blood pressure of said subject, a local blood volume of said subject, a cardiac sound, and skin displacements caused by pulsatile blood flow in the vasculature of said subject.

4. The method according to claim 1, wherein said REM is determined based on a number of points in a vicinity of an identity line of said Poincare plot.

5. The method according to claim 1, further comprising calculating a plurality of moments with respect to a predetermined line along said Poincare plot, each of said plurality of moments being calculated within a predetermined time-window.

6. The method according to claim 1, further comprising accessing an annotated library of balances and searching for balances similar to said at least one calculated balance so as to determine said REM sleep.

7. The method according to claim 1, further comprising obtaining a time-frequency decomposition of said IBI series and calculating at least one frequency parameter from said time-frequency decomposition, wherein said determining said REM sleep is based, at least in part, on said at least one frequency parameter.

8. The method according to claim 7, further comprising determining at least one sleep stage selected from the group consisting of light-sleep (LS) and slow wave sleep (SWS).

9. The method according to claim 1, wherein said signal is a radar signal.

10. The method of claim 1, further comprising:
    operating said electronic computing circuitry for:
    obtaining a time-frequency decomposition of said IBI series; and
    determining at least one sleep stage selected from the group consisting of light-sleep (LS) and slow wave sleep (SWS), based on said time-frequency decomposition.

11. The method according to claim 10, wherein said signal is generated by converting a wave selected from the group consisting of a mechanical wave, an optical wave and an electromagnetic wave into an electrical signal.

12. The method according to claim 10, wherein said signal is indicative of at least one of: a local blood pressure of said subject, a local blood volume of said subject, a cardiac sound, and skin displacements caused by pulsatile blood flow in the vasculature of said subject.

13. A system for determining a REM sleep of the sleeping subject, the system comprising:
    a sensing device having a circuit adapted for converting a wave selected from the group consisting of a mechanical wave, an optical wave and an electromagnetic wave into an electrical signal indicative of heart beats of the sleeping subject, and storing said signal in a computer readable memory, said signal being other than an electrocardiogram (ECG) signal;
    a data processor configured for receiving said signal, extracting from said a series of inter-beat intervals (IBI), constructing a Poincare plot of said IBI series, storing said Poincare plot in a computer readable memory, calculating, for a moving window in time, balance between odd and even quantiles in said Poincare plot, and determining a REM sleep of the sleeping subject based on said balance wherein said quantiles are quartiles; and
    a display device, remote from said sensing device for displaying information pertaining to said REM sleep.

14. The system according to claim 13, wherein said sensing device is configured for sensing at least one of: a local blood pressure of said subject, a local blood volume of said subject, a cardiac sound, and skin displacements caused by pulsatile blood flow in the vasculature of said subject.

15. The system according to claim 13, wherein said sensing device is selected from the group consisting of a plethysmograph, a microphone, a radar, an accelerometer and a displacement sensing device.

16. The system according to claim 13, wherein said REM is determined based on a number of points in a vicinity of an identity line of said Poincare plot.

17. The system according to claim 13, wherein said data processor is configured for calculating a plurality of moments with respect to a predetermined line along said Poincare plot, each of said plurality of moments being calculated within a predetermined time-window.

18. The system according to claim 13, wherein said data processor is configured for accessing an annotated library balances and searching for balances similar to said at least one calculated balance so as to determine said REM sleep.

19. The system according to claim 13, wherein said data processor is configured for obtaining a time-frequency decomposition of said IBI series and calculating at least one frequency parameter from said time-frequency decomposition, wherein said determining said REM sleep is based, at least in part, on said at least one frequency parameter.

20. The system according to claim 19, wherein said data processor is configured for determining at least one sleep stage selected from the group consisting of light-sleep (LS) and slow wave sleep (SWS).

21. A method of determine a REM sleep of the sleeping subject, the method comprising:

by a sensing device having a circuit, converting a wave selected from the group consisting of a mechanical wave, an optical wave and an electromagnetic wave into an electrical signal indicative of heart beats of the sleeping subject, and storing said signal in a computer readable memory, said signal being other than an electrocardiogram (ECG) signal; and receiving said signal by electronic computing circuitry;

by said electronic computing circuitry, extracting from said signal a series of inter-beat intervals (IBI), constructing a Poincare plot of said IBI series, storing said Poincare plot in a computer readable memory, calculating, for a moving window in time, at least one Poincare parameter describing said Poincare plot, and writing said at least one Poincare parameter onto a data storage medium;

by said electronic computing circuitry, receiving said at least one Poincare parameter from said data storage medium, calculating balance between odd and even quantiles in said Poincare plot, and determining a REM sleep of the sleeping subject based on said balance, wherein said quantiles are quartiles; and displaying information pertaining to said REM sleep on a display.

* * * * *